United States Patent
Leavesley

(10) Patent No.: US 10,393,964 B2
(45) Date of Patent: Aug. 27, 2019

(54) SPECTRAL ILLUMINATION DEVICE AND METHOD

(71) Applicant: UNIVERSITY OF SOUTH ALABAMA, Mobile, AL (US)

(72) Inventor: Silas Leavesley, Mobile, AL (US)

(73) Assignee: THE UNIVERSITY OF SOUTH ALABAMA, Mobile, AL (US)

(*) Notice: Subject to any disclaimer, the term of this patent is extended or adjusted under 35 U.S.C. 154(b) by 0 days.

(21) Appl. No.: 14/419,855

(22) PCT Filed: Aug. 6, 2013

(86) PCT No.: PCT/US2013/053787
§ 371 (c)(1),
(2) Date: Feb. 5, 2015

(87) PCT Pub. No.: WO2014/025777
PCT Pub. Date: Feb. 13, 2014

(65) Prior Publication Data
US 2015/0185421 A1 Jul. 2, 2015

Related U.S. Application Data

(60) Provisional application No. 61/742,303, filed on Aug. 7, 2012.

(51) Int. Cl.
*G02B 6/00* (2006.01)
*G01N 21/00* (2006.01)
(Continued)

(52) U.S. Cl.
CPC .......... *G02B 6/2804* (2013.01); *A61B 1/0638* (2013.01); *A61B 1/0669* (2013.01); *A61B 1/07* (2013.01); *G01N 21/55* (2013.01); *G01N 21/6456* (2013.01); *G02B 6/4249* (2013.01); *G02B 6/4296* (2013.01); *A61B 1/043* (2013.01); *A61B 1/0646* (2013.01); *A61B 1/0684* (2013.01);
(Continued)

(58) Field of Classification Search
USPC ............................ 356/432–448, 450–458
See application file for complete search history.

(56) References Cited

U.S. PATENT DOCUMENTS

| | | | | |
|---|---|---|---|---|
| 3,453,036 A | * | 7/1969 | Koester | G02B 6/2804 385/39 |
| 3,825,336 A | * | 7/1974 | Reynolds | G03B 27/73 353/84 |

(Continued)

FOREIGN PATENT DOCUMENTS

DE    102008027251 A1    3/2010

OTHER PUBLICATIONS

Search Report in international application PCT/US2013/053787 issued by ISA/KR.

(Continued)

*Primary Examiner* — Shawn Decenzo
*Assistant Examiner* — Jarreas C Underwood
(74) *Attorney, Agent, or Firm* — J.M. Robertson, LLC

(57) ABSTRACT

An illumination device and method including multiple illumination sources such as LEDs, lasing diodes or the like operatively connected to a multi-branch light guide adapted to collect and co-align beams from the illumination sources for delivery of high intensity, spatially uniform illumination.

23 Claims, 3 Drawing Sheets

(51) Int. Cl.

| | | |
|---|---|---|
| G02B 6/28 | (2006.01) | |
| G02B 6/42 | (2006.01) | |
| G01N 21/55 | (2014.01) | |
| G01N 21/64 | (2006.01) | |
| A61B 1/06 | (2006.01) | |
| A61B 1/07 | (2006.01) | |
| A61B 1/04 | (2006.01) | |

(52) U.S. Cl.
CPC ........... *G01N 2021/6484* (2013.01); *G01N 2201/062* (2013.01); *G01N 2201/0612* (2013.01); *G01N 2201/08* (2013.01)

(56) References Cited

U.S. PATENT DOCUMENTS

| | | | | | |
|---|---|---|---|---|---|
| 4,232,385 | A | * | 11/1980 | Hara | H04J 14/02 385/45 |
| 4,578,791 | A | * | 3/1986 | Chen | G02B 6/2804 372/108 |
| 4,725,131 | A | * | 2/1988 | Goodwin | G02B 6/42 372/50.1 |
| 4,760,250 | A | * | 7/1988 | Loeppert | G01N 21/7703 250/205 |
| 4,932,747 | A | * | 6/1990 | Russell | G02B 6/04 219/121.6 |
| 5,031,078 | A | * | 7/1991 | Bornhorst | G02B 6/00 362/552 |
| 5,195,162 | A | * | 3/1993 | Sultan | G01D 5/268 356/614 |
| 5,301,090 | A | * | 4/1994 | Hed | G02B 6/001 362/558 |
| 5,394,492 | A | * | 2/1995 | Hwang | G02B 6/32 385/118 |
| 5,465,194 | A | * | 11/1995 | Currie | B60Q 1/0011 340/468 |
| 5,781,678 | A | * | 7/1998 | Sano | G02B 6/3878 226/7 |
| 6,217,201 | B1 | * | 4/2001 | Hulse | B60Q 1/0011 362/489 |
| 6,411,323 | B1 | * | 6/2002 | Waarts | G02B 6/29319 347/241 |
| 6,655,825 | B2 | * | 12/2003 | Muthu | G02B 6/0028 362/555 |
| 6,733,166 | B2 | * | 5/2004 | Hulse | B60Q 3/004 362/33 |
| 6,843,591 | B1 | * | 1/2005 | Peng | G02B 6/0006 359/618 |
| 7,128,431 | B2 | * | 10/2006 | Ludewig | G02B 6/04 362/23.09 |
| 7,168,862 | B2 | * | 1/2007 | Qi | A47G 33/06 362/553 |
| 7,245,804 | B2 | * | 7/2007 | Teramura | G02B 27/0994 372/50.12 |
| 7,400,801 | B1 | * | 7/2008 | Tong | G02B 6/1228 385/14 |
| 7,460,755 | B2 | * | 12/2008 | Bruesselbach | G02B 6/04 385/115 |
| 7,852,484 | B2 | * | 12/2010 | Teramura | G01N 21/4795 356/479 |
| 8,251,896 | B2 | * | 8/2012 | Robinson | A61B 1/00009 600/121 |
| 8,439,526 | B2 | * | 5/2013 | Brusilovsky | F21K 9/13 362/231 |
| 2002/0102058 | A1 | | 8/2002 | Hulse | |
| 2005/0256516 | A1 | * | 11/2005 | Boutoussov | A61B 18/22 606/16 |
| 2006/0083461 | A1 | | 4/2006 | Takahashi | |
| 2008/0140325 | A1 | | 6/2008 | Teramura | |
| 2008/0292243 | A1 | * | 11/2008 | Izumo | G08C 23/06 385/31 |
| 2009/0012369 | A1 | | 1/2009 | Robinson et al. | |
| 2010/0045954 | A1 | | 2/2010 | Onvlee | |

OTHER PUBLICATIONS

International Preliminary Report on Patentability in international application PCT/US2013/053787.
EPO Examination Report for counterpart application EP2882994.
Fercher et al. Optical Coherence Tomography—Principles and Applications; Reports on Progress in Physics, Institute of Physics Publishing, Issue 66, Jan. 2003, pp. 239-303.

* cited by examiner

SPECTRAL ILLUMINATION DEVICE AND METHOD

CROSS-REFERENCE TO RELATED APPLICATIONS

This application is a National Phase of International Application Number PCT/US2013/053787, filed Aug. 6, 2013 and claims the benefit of, and priority from, U.S. provisional application 61/742,303 having a filing date of Aug. 7, 2012.

TECHNICAL FIELD

This disclosure relates to illumination and optical devices, and more particularly, to an apparatus adapted to provide high-power illumination across multiple wavelengths through coalignment of the output from multiple broad band or narrow band illumination sources along a common guide. The present disclosure also relates to a method to co-align multiple illumination sources of substantially the same wavelength profile to obtain a higher power output. The present disclosure also relates to a method to combine outputs from multiple illumination sources to provide a hyperspectral illumination source suitable for use in imaging.

BACKGROUND

Reflectance and Fluorescence imaging are used in numerous medical and research applications. By way of example only, White light endoscopy (WLE) is the standard approach for colon cancer screening. However, traditional WLE relies on native tissue contrast (reflectance), and lacks specificity. Autofluorescence imaging (AFI) and narrow-band imaging (NBI) have been applied in an effort to increase the ability to detect cancers of the colon. These approaches have, in some cases, shown increased sensitivity and specificity. However, various large-scale studies have shown negligible improvements over WLE. The low specificity is largely due to insufficient information in the one or two wavelength bands acquired. Accordingly, it is simply not possible to detect changes in the fluorescence associated with many biomarkers in the presence of autofluorescence from healthy tissue using AFI or NBI.

Previous studies have demonstrated that tumors have reflectance and/or fluorescence spectra that are different from surrounding tissue, and that sampling this spectrum can result in increased sensitivity and specificity. However, heretofore, there has been no suitable hyperspectral illumination device providing illumination with multiple, discrete narrow wavelength bands over a wide spectral range for practical use in reflectance or fluorescence imaging of multiple biomarkers.

Briefly, fluorescence is a chemical process wherein light of a specific wavelength shined upon a fluorescent molecule causes electrons to be excited to a high energy state in a process known as excitation. These electrons remain briefly in this high energy state, for roughly a nanosecond, before dropping back to a low energy state and emitting light of a lower wavelength. This process is referred to as fluorescent emission, or alternatively as fluorescence.

In a typical fluorescence imaging application, one or more types of fluorescent materials or molecules (sometimes referred to as fluorescent dyes) are used, along with an illuminator apparatus that provides the exciting wavelength, or wavelengths. Different fluorescent molecules can be selected to have visually different emission spectra. Since different fluorescent molecules typically have different excitation wavelengths, they can be selectively excited so long as the bandwidth of the excitation light for one fluorescent molecule does not overlap the excitation wavelengths of other fluorescent molecules that are present in the body being imaged. Therefore the excitation light should ideally have well defined bandwidths. Moreover, it may be desirable to use an intense light so as to increase the chances of the fluorescence process occurring.

Traditional fluorescence illuminators have relied on metal halide arc lamp bulbs such as Xenon or Mercury bulbs, as light sources. The broad wavelength spectrum produced by these lamps when combined with specific color or band pass filters allows for the selection of different illumination wavelengths. However, this wavelength selection and light shaping process is highly energy inefficient. In this regard, selecting only a relatively small portion of the wavelength spectrum produced by the Xenon or Mercury bulb results in the vast majority of the light output from the lamp being unused. Moreover, the wavelength selection or band pass filters are costly, especially when placed on a mechanical rotating wheel in typical multiple-wavelength applications.

When using metal halide arc lamp bulbs, the speed with which different wavelengths can be selected is limited by the mechanical motion of moving various filters into place. In addition to the sluggishness and unreliability of filter wheels, as well as energy coupling inefficiency, metal halide arc lamps are also hampered by the limited lifetime of the bulb. The intensity of the light output declines with bulb use and once exhausted, the user has to undergo a complicated and expensive process of replacing the bulb and subsequently realigning the optics without any guarantee that the illuminator will perform as before. These disadvantages make acquiring consistent results difficult and inconvenient for users who must deal with the variable output of the bulbs, and who must either be trained in optical alignment or call upon professionals when a bulb needs to be replaced.

A light-emitting diode (LED) is a solid state, semiconductor based light source. Modern LEDs are available to provide discrete emission wavelengths ranging from ultraviolet (UV) to infrared (IR). The use of LEDs as light sources overcomes numerous limitations of metal halide arc lamps. By way of example only, the lifetime of an LED is typically rated at well over 10,000 hours which is much greater than that of metal halide arc lamps. Moreover, the power output varies negligibly over the full life of the LED. In addition, the bandwidth of the spectral output of an LED chip is typically narrow (<30 nm) which can reduce or eliminate the need for additional band pass filters in a fluorescence application. Moreover, the intensity of the output light from an LED can be quickly and accurately controlled electronically by varying the current through the LED chip(s), whereas in metal halide illuminators, the output intensity of the bulb is constant and apertures or neutral density filters are used to attenuate the light entering the microscopy.

In the past, the number of LED light sources which could be aligned was limited to about 4 or 5 due to the relatively long optical paths required to combine the beams from the multiple chips or modules which are spatially separated using free space optics. This alignment difficulty has substantially limited the application of LED light sources in imaging applications since the desired high intensity for such applications is difficult to achieve. Attempts to address this deficiency have incorporated the use of additional optical elements such as lenses, mirrors and the like for each wavelength. However, the use of such optical elements has practical limitations due to their negative impact on intensity and uniformity of the treated light beams. These issues have limited the practical use of LED-based illuminators in reflectance and fluorescence imaging applications which require light that is both intense and spatially uniform.

Accordingly, there is a continuing need for an illumination device adapted to efficiently align light output from multiple wide band or narrow-band illumination sources such as LEDs, lasing diodes, or the like for delivery of high intensity, spatially uniform illumination to a field of observation. By way of example only, and not limitation, such an illumination device may be used in a hyperspectral reflectance or fluorescence imaging endoscope or microscope that can reveal pathology specific changes in the structure and molecular composition of tissues, allowing early detection and differentiation of pathological processes in the colon or other tissues.

SUMMARY OF THE DISCLOSURE

The present disclosure provides advantages and alternatives over the prior art by providing an illumination device including multiple illumination sources such as LEDs, lasing diodes or the like operatively connected to a multi-branch light guide adapted to collect and coalign beams from the illumination sources for delivery of high intensity, spatially uniform illumination.

Other objects and advantages of the carrying device will become apparent from a description of certain preferred embodiments thereof which are described and shown in the drawings.

Figure 1:
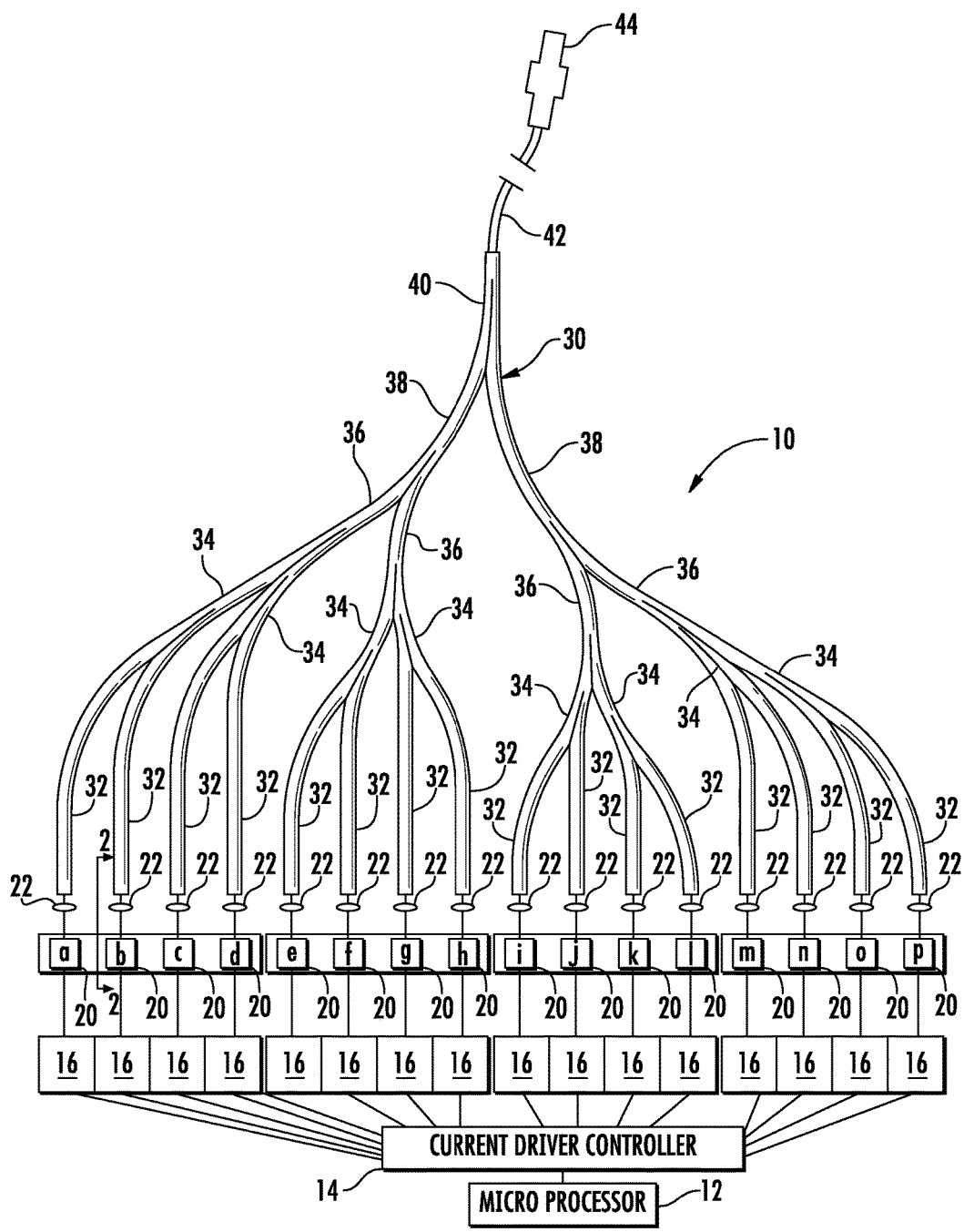
FIG. 1 is a schematic view of an exemplary illumination system consistent with the present disclosure adapted for operative connection to a multiplicity of LEDs, lasing diodes or other illumination sources.

Before the exemplary embodiments are illustrated and explained in detail, it is to be understood that the invention is in no way limited in its application or construction to the details and the arrangements of the components set forth in the following description or illustrated in the drawings. Rather, the invention is capable of other embodiments and of being practiced or being carried out in various ways. Also, it is to be understood that the phraseology and terminology used herein are for purposes of description only and should not be regarded as limiting. The use herein of terms such as "including" and "comprising" and variations thereof is meant to encompass the items listed thereafter and equivalents thereof as well as additional items and equivalents thereof.

DETAILED DESCRIPTION OF PREFERRED EMBODIMENTS

Reference will now be made to the drawings, wherein like reference numerals are used to designate like elements in the various views. FIG. 1 is a schematic view of an exemplary hyperspectral illumination system 10 adapted to coalign light emissions from a multiplicity of light emitting diodes, lasing diodes or other solid state light sources. As will be appreciated, while the illustrated, exemplary illumination system 10 incorporates sixteen light inlet positions, adapted for operative connection to light sources, it is likewise contemplated that any greater or lesser number of inlet positions may be used if desired.

As illustrated, in the exemplary system, a programmable microprocessor 12, such as general purpose computer, or the like, may be provided to deliver instructions to a current driver controller 14 operatively linked to one or more current drivers 16. As will be readily appreciated by those of skill in the art, the current drivers 16 may deliver current at varying levels based on instructions received from the controller 14. Thus, based on instructions from the microprocessor 12, the current drivers 16 may deliver a range of currents as may be desired.

Figure 2:
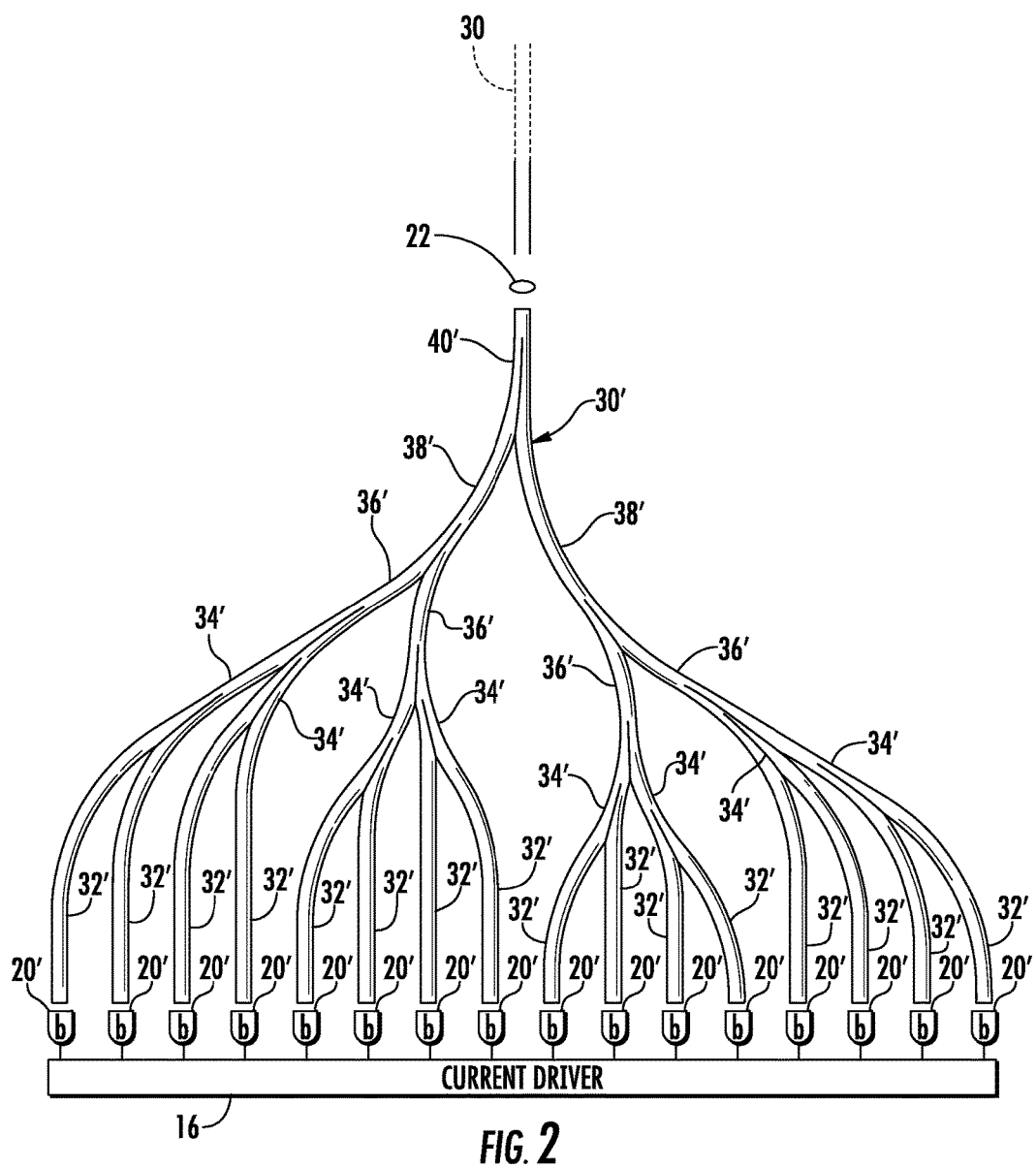
FIG. 2 is a schematic view taken generally along line 2-2 in FIG. 1.
Figure 3:
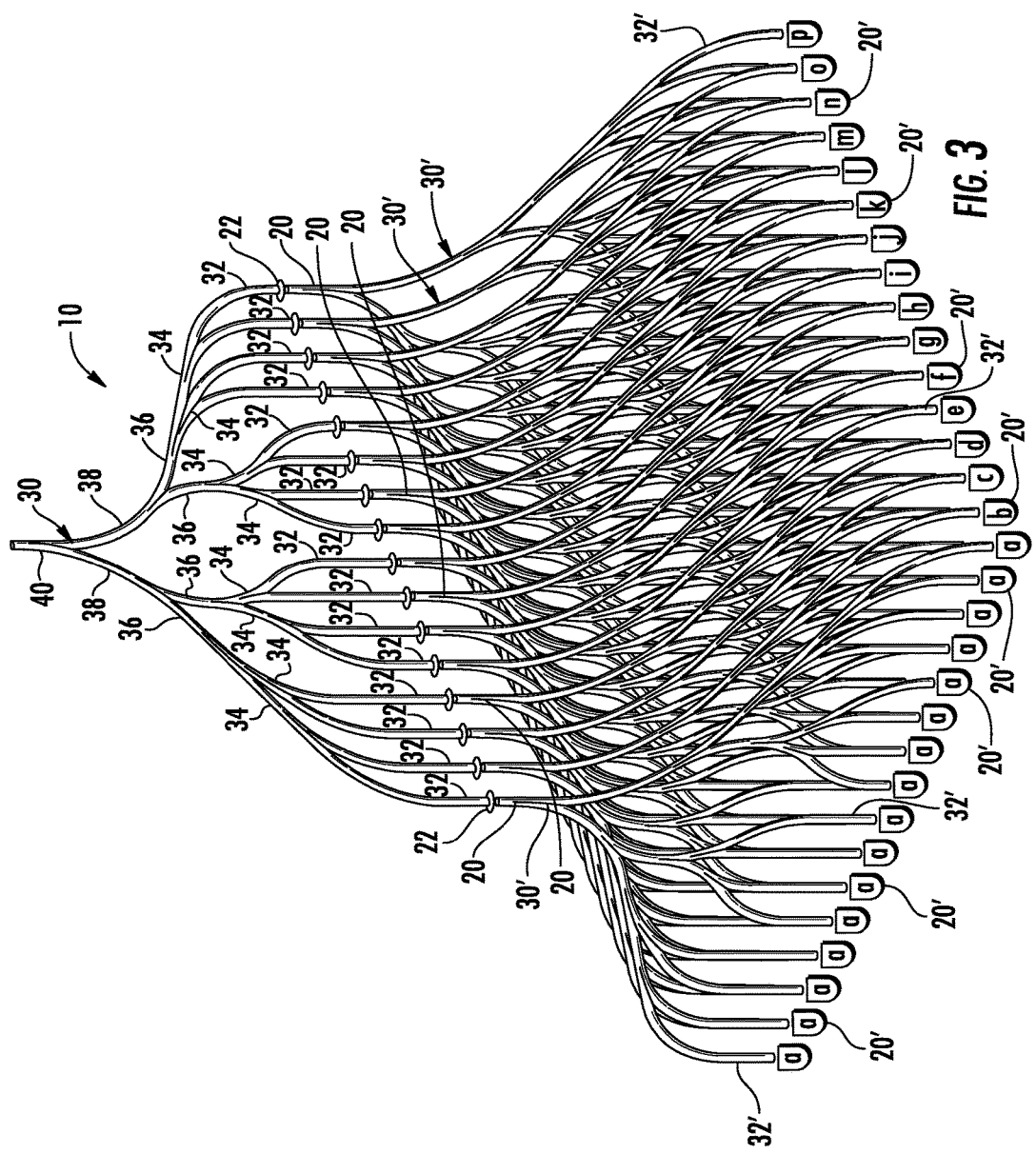
FIG. 3 is a schematic perspective view of the exemplary illumination system of FIG. 1.

In the illustrated exemplary arrangement, the current drivers 16 may each transmit current to a plurality of discrete light sources 20 (labeled as a-p). By way of example only and not limitation, in the illustrated exemplary arrangement, each of the light sources 20 may be a single light emitting element or may be a suitable light guide as will be described hereinafter which collects and aligns light emissions from multiple light emitting elements. In accordance with one exemplary practice, the light sources 20 each may be operatively linked to an array of multiple light emitting elements 20' such as LEDs, lasing diodes or other broad band or narrow wavelength band light sources of substantially the same wavelength character (FIGS. 2 and 3). Each array may, in turn, be operatively linked to a current driver 16 such that all light emitting elements in a given array may be activated and deactivated simultaneously. It is also contemplated that each individual light emitting element 20' may be operated substantially independently if desired. Of course, any number of arrays may be used as desired. Moreover, it is also contemplated that virtually any number of layers of arrays may be used as desired restricted only by space limitations.

Referring now jointly to FIGS. 1-3, in the illustrated exemplary construction each of the light sources 20 may be a multi-branch light guide operatively connected to a multiplicity of light emitting elements 20' having a common wavelength emission character. That is, the light source 20, labeled as "a" in FIG. 1 may be a multi-branch light guide operatively connected to a multiplicity of light emitting elements 20' having a common wavelength emission character $\lambda_1$. Likewise the light source 20, labeled as "b" in FIG. 1 may be a multi-branch light guide operatively connected to a multiplicity of light emitting elements 20' having a common wavelength emission character $\lambda_2$. The light source 20, labeled as "o" in FIG. 1 may be a multi-branch light guide operatively connected to a multiplicity of light emitting elements 20' having a common wavelength emission character character $\lambda_{n-1}$. The light source 20, labeled as "p" in FIG. 1 may be a multi-branch light guide operatively connected to a multiplicity of light emitting elements 20' having a common wavelength emission character $\lambda_n$ where n is equal to the number of different emission wavelengths supplied to the illumination system by the light sources 20. Of course, in the illustrated exemplary system, n is equal to 16. However, any number of different emission wavelengths may be used as desired.

As noted previously, each array of light emitting elements of common wavelength may be coupled to a common current driver 16. Thus, each of the light sources at a given wavelength may be activated and deactivated simultaneously if desired. As will be described further hereinafter, such simultaneous activation of multiple light sources with common wavelengths coupled to a common light guide provides an additive benefit resulting in a final emission from the light guide of greatly enhanced power at the defined wavelength.

It is to be understood that any number of arrays of light sources may be utilized. Likewise, each array operatively connected to a current driver 16 may incorporate light emitting elements 20' of two or more different emission characters if desired. It is also contemplated that two or more light sources 20 may have substantially the same emission wavelength character. Thus, in accordance with one contemplated arrangement, each of the light sources 20 in the illumination system 10 may have substantially the same emission wavelength character. In accordance with another contemplated arrangement, each of the light sources 20 in the illumination system 10 may have a substantially different emission wavelength character. It is likewise contemplated that there may be some duplication of emission wavelength character from the various light sources 20 but without uniformity of emission wavelength character from all of the light sources 20.

The emission wavelengths generated by the light sources 20 may be controlled by the user in two ways. First, the light emitting elements 20' will themselves have a characteristic peak wavelength emission. In this regard, commercially available LEDs are available with defined emission peaks ranging from ultraviolet through IR wavelengths. Thus, by selection of a defined light emitting element with a known peak wavelength character, the emission wavelength from that light source may be established. Second, LEDs may be pulsed at rapid speed to permit wavelength switching if desired.

Regardless of the selection of light source character, it may be desirable to utilize the peak wavelength from the emission generated by each light source 20. In this regard, while an LED may provide a relatively narrow wavelength band emission, it nonetheless may be useful to further narrow the wavelength band around the peak of the light source so as to reduce the possibility of overlapping bands and to promote proper fluorescent excitation during imaging use. In accordance with one exemplary practice, such wavelength band narrowing may be achieved by placement of optional band pass filters 22 at the outlets of the light sources 20. By way of example only, and not limitation, it has been found that an optional 10-15 nm band pass filter corresponding to the peak wavelength for the opposing light source 20 may provide a desirable filter level. Of course, greater or lesser width band pass filters may likewise be used if desired.

The number and character of light emitting elements in the illumination system 10 will dictate the achievable optical power for a given wavelength in an imaging environment. By combining multiple LEDs, lasing diodes, or other light sources with common peak wavelengths, optical power levels for those wavelengths can be raised. By way of example only, and not limitation, it is contemplated that a delivered optical power of at least 20 mW per band is achievable and may be desirable for many excitation imaging applications.

It has been found that a solid light guide 30 also referred to as a light pipe of exponential duplicating branched character may be used to efficiently receive and transmit outputs from multiple light sources and to coalign those outputs along a common transmission trunk. Likewise, in the exemplary system illustrated in FIG. 3, secondary solid light guides 30' of substantially similar geometry may be used to collect and to coalign outputs from multiple light emitting elements 20' for subsequent delivery to the solid light guide 30. As will be appreciated, by collecting the outputs from multiple light emitting elements 20' and coaligning those outputs along a common trunk, the optical power output delivered to the solid light guide 30 may be greatly magnified. In this regard, while two layers of light guides (30 and 30') are shown in stacked relation, it is contemplated that virtually any number of layers may be used such that a nearly limitless number of light emitting elements may be accommodated.

Referring now jointly to FIGS. 1 and 2, in the illustrated, exemplary construction, the light guides 30, 30' are characterized by a branched construction in which sixteen proximal branches 32, 32' each defines an acceptance port for a discrete light input (either from a light source 20 or from an individual light emitting element 20'). In this configuration, the proximal branches 32, 32' each merge with a single adjacent proximal branch to form a first set of eight intermediate branches 34, 34'. Each member of the first set of intermediate branches then merges with an adjacent intermediate branch to yield a second set of four intermediate branches 36, 36'. Each member of the second set of intermediate branches then merges with an adjacent intermediate branch to yield a third set of two intermediate branches 38, 38'. Finally, in the illustrated exemplary construction, the two members of the third set of intermediate branches merge with one another to yield a single main trunk 40, 40'. As will be appreciated, in the illustrated light guides 30, 30' this progressive exponential merger may be defined by the general geometric regression:

$$2^n, 2^{n-1}, \ldots, 2^1, 2^0$$

where the value of n is selected to yield the number of desired input positions for the light sources 20. By way of example only, in the illustrated exemplary construction of FIG. 1, n=4 so as to yield the illustrated sixteen operative input positions. Of course, any larger or smaller number of inputs may be used as desired. It is also contemplated that in some embodiments three or more branches may merge at positions along the light guides until ultimately terminating at a single trunk. Thus, the base 2 regression as outlined above is in no way exclusive.

As shown, at the intersection between the merging branches it may be desirable for the slope of centerlines running along the merging branches to be substantially aligned at the point of intersection. By way of example only, it may be desirable for the intersection of tangents to the centerlines to be at angles of between zero (i.e. parallel) to not more than about 30 degrees such that sharp intersecting angles are substantially avoided. It has also been found that it may be desirable for the radius of curvature for each of the intermediate branches to be not less than about 60 mm and more preferably about 70 mm or greater. These general guidelines for merging multiple branches have been found to reduce power loss while promoting coalignment. In this regard, a majority of the branches transmit at over 35% of input which is an efficiency that would be unattainable using traditional fiber bundles. In addition, the ability to combine the output from multiple LEDs at each wavelength is used to compensate for light-guide coupling losses. Accordingly, final output power levels of 20 mW or greater may be readily achieved despite any losses even if low power LEDs or other originating light sources are used.

In accordance with one exemplary practice, the light guides 30, 30' may each be formed as a unitary structure from a material such as polycarbonate or the like. According to one exemplary embodiment, the trunk and all branches may be substantially circular with equal cross sectional diameters. By way of example only, and not limitation, a cross-sectional diameter of about 5 mm with the branches merging according to the practices as outlined above has been found to provide effective transmission of the light input. In this regard, light is channeled or transmitted along the longitudinal axis of each branch by total internal reflection such that light is prevented from passing from inside the light guide to the outside. Total internal reflection occurs when light impinges on an interface between the light guide and the surrounding atmosphere at an angle that is greater than a critical angle. The critical angle is a function of the indices of refraction for the medium of the light guide and the medium of the surrounding atmosphere.

As illustrated, in accordance with one exemplary practice, the main trunk 40 of the output light guide 30 may be operatively connected to a fiber optic cable 42 which, in turn, is connected to an imaging device 44 such as a small diameter endoscope, a microscope or the like. During use, a number of light sources 20 as previously described having desired wavelength emission character may be operatively attached at the ends of the proximal branches 32 of the output light guide. In this regard, it is contemplated that the light sources 20 may be individually connected or may be supported in discrete modules housing multiple light source elements. The outputs from individual light emitting elements of similar character are combined as adjacent branches which merge thereby magnifying the optical power associated with each defined wavelength.

During use of the illumination system 10, one or more arrays of light emitting elements of defined wavelength may be activated such that the coaligned light beams of magnified optical power may be transmitted through the light guide 30 to the imaging device. In this regard, while the merger and coalignment of the light beams from discrete light emitting elements increases the optical power in the delivered light output relative to the originating elements, the wavelength character remains unaltered.

At the imaging device 44, the defined wavelength emission may be used for fluorescence excitation, reflectance, or some combination of fluorescence and reflectance. The wavelength character of the light delivered to the imaging device may be rapidly changed by activating and deactivating selected light sources or combinations of light sources. By way of example only, a wavelength $\lambda_1$ may be activated for delivery to the imaging device to generate a first image for a tissue or other target material followed by activation of wavelength $\lambda_5$ to generate a second, different image for the tissue or other target material. Since different materials react differently to different wavelength excitations, the ability to very rapidly switch wavelengths by activating and deactivating groups of light emitting elements permits the development of multiple different images detailing different features of a target material.

An illumination system 10 consistent with the present disclosure may be used in a number of imaging devices including, by way of example only, endoscopes, microscopes, opthalmoscopes, colposcopes, small animal imagers, industrial machine vision devices and the like. An illumination system 10 consistent with the present disclosure also may be used in a number of or non-imaging applications including chemical detection devices, bacterial and other types of molecular screening devices useful in research, clinical use, and the like.

By way of example only, and not limitation, according to one contemplated application, a tissue may be scanned using a series of different excitation wavelengths to identify the presence of abnormal cells which fluoresce at different wavelengths from normal cells. Moreover, since different kinds of abnormal cells will fluoresce at different wavelengths, not only the presence, but also the character of the abnormal cells may be determined. By cycling through a series of discrete wavelengths, different types of abnormal cells with different fluorescence excitation characteristics may be identified and imaged.

By way of further example, in accordance with another contemplated application, the light sources 20 in an illumination system 10 consistent with the present disclosure may be pulsed using an arbitrary waveform or be strobed in combination with a delayed detection to measure a time decay of fluorescence (fluorescence lifetime) of a target material. This may be achieved either through frequency-domain with sinusoidal illumination and detection or in a time-domain with pulsed illumination and delayed detection. Accordingly, the illumination system 10 permits both spectral measurements and fluorescence lifetime measurements to be taken simultaneously. As will be appreciated, this provides enhanced information regarding the target material and may be particularly useful for applications such as microscopy and clinical diagnosis.

Of course, variations and modifications of the foregoing are within the scope of the present invention. Thus, it is to be understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention. The claims are to be construed to include alternative embodiments and equivalents to the extent permitted by the prior art.

The invention claimed is:

1. An illumination system adapted to provide a plurality of coaligned light beams of different wavelength character for use in selective fluorescence or reflectance of a target being imaged, the illumination system comprising: a plurality of selectively activatable light sources characterized by defined intrinsic peak wavelength light emissions; at least a first multi-branch solid light guide of unitary, hard plastic construction, the solid light guide comprising a main trunk, a plurality of proximal branches defining inlets adapted to receive the light emissions from the light sources, and at least one set of intermediate branches disposed between the proximal branches and the main trunk, wherein at least a first one of the proximal branches merges with a second one of the proximal branches to form a first intermediate branch and at least a third one of the proximal branches merges with a fourth one of the proximal branches to form a second intermediate branch, wherein light emissions transmitted by the first one of the proximal branches are combined with the light emissions transmitted by the second one of the proximal branches within the first intermediate branch and wherein light emissions transmitted by the third one of the proximal branches are combined with the light emissions transmitted by the fourth one of the proximal branches within the second intermediate branch such that the intermediate branches carry combined light emissions from the proximal branches towards the main trunk; and an imaging or optical device operatively connected to the main trunk for transmission of coaligned light emissions from the light sources at a magnified power level greater than the power level of the light emissions from the individual selectively activatable light sources and wherein the magnified power level is suitable for selective fluorescence or reflectance of the target.

2. The illumination system as recited in claim 1, wherein the imaging or optical device is selected from the group consisting of endoscopes, microscopes, opthalmoscopes, colposcopes, small animal imagers, industrial machine vision devices and combinations thereof.

3. The illumination system as recited in claim 1, wherein the first one of the proximal branches merges with the second one of the proximal branches at an angle of between zero and 30 degrees.

4. The illumination system as recited in claim 3, wherein the third one of the proximal branches merges with the fourth one of the proximal branches at an angle of between zero and 30 degrees.

5. The illumination system as recited in claim 1, wherein one or more of the selectively activatable light sources comprises a secondary solid light guide comprising a plurality of inlets adapted to receive light emissions from selectively activatable light emitting elements.

6. The illumination system as recited in claim 5, wherein the secondary solid light guide comprises a main trunk, a plurality of proximal branches defining inlets adapted to receive the light emissions from the light emitting elements, and at least one set of intermediate branches disposed between the proximal branches and the main trunk.

7. The illumination system as recited in claim 5, wherein the light emitting elements are selected from the group consisting of light emitting diodes, lasing diodes and combinations thereof.

8. The illumination system as recited in claim 1, wherein one or more of the selectively activatable light sources comprises an individual light emitting element.

9. The illumination system as recited in claim 8, wherein the individual light emitting element is selected from the group consisting of light emitting diodes and lasing diodes.

10. The illumination system as recited in claim 1, further comprising a plurality of band pass filters adapted to narrow the light emissions from the first plurality of selectively activatable light sources to a band of not greater than 15 nm.

11. The illumination system as recited in claim 1, wherein the imaging or optical device is a chemical detection device.

12. The illumination system as recited in claim 1, wherein the imaging or optical device is a bacterial screening device.

13. The illumination system as recited in claim 1, wherein the imaging or optical device is a molecular screening device.

14. An illumination system adapted to provide a plurality of coaligned light beams of different wavelength character for use in selective fluorescence or reflectance of a target being imaged, the illumination system comprising: a plurality of selectively activatable light sources characterized by defined intrinsic peak wavelength light emissions; a plurality of band pass filters adapted to narrow the light emissions from the light sources to a band of not greater than 15 nm; at least a first multi-branch solid light guide of unitary, hard plastic construction, the solid light guide comprising a main trunk, a plurality of proximal branches defining inlets adapted to receive the light emissions from the light sources, and at least one set of intermediate branches disposed between the proximal branches and the main trunk, wherein at least a first one of the proximal branches merges with a second one of the proximal branches at an angle of between zero and 30 degrees to form a first intermediate branch and at least a third one of the proximal branches merges with a fourth one of the proximal branches at an angle of between zero and 30 degrees to form a second intermediate branch, wherein light emissions transmitted by the first one of the proximal branches are combined with the light emissions transmitted by the second one of the proximal branches within the first intermediate branch and wherein light emissions transmitted by the third one of the proximal branches are combined with the light emissions transmitted by the fourth one of the proximal branches within the second intermediate branch such that the intermediate branches carry combined light emissions from the proximal branches towards the main trunk; and an imaging or optical device operatively connected to the main trunk for transmission of coaligned light emissions from the light sources at a magnified power level of not less than 20 mW, the magnified power level being greater than the power level of the light emissions from the individual selectively activatable light sources and wherein the magnified power level is suitable for selective fluorescence or reflectance measurements of the target.

15. The illumination system as recited in claim 14, wherein the imaging or optical device is selected from the group consisting of endoscopes, microscopes, opthalmoscopes, colposcopes, small animal imagers, industrial machine vision devices and combinations thereof.

16. The illumination system as recited in claim 14, wherein the radius of curvature for each of the intermediate branches is 60 mm or greater.

17. The illumination system as recited in claim 16, wherein the radius of curvature for each of the intermediate branches is 70 mm or greater.

18. The illumination system as recited in claim 14, wherein one or more of the selectively activatable light sources comprises an individual light emitting element.

19. The illumination system as recited in claim 18, wherein the individual light emitting element is selected from the group consisting of light emitting diodes and lasing diodes.

20. The illumination system as recited in claim 14, wherein one or more of the selectively activatable light sources comprises a secondary solid light guide comprising a plurality of inlets adapted to receive light emissions from selectively activatable light emitting elements.

21. The illumination system as recited in claim 20, wherein said secondary solid light guide comprises a main trunk, a plurality of proximal branches defining inlets adapted to receive the light emissions from the light emitting elements, and at least one set of intermediate branches disposed between the proximal branches and the main trunk, wherein the intermediate branches are formed by two or more proximal branches merging at an angle of between zero and 30 degrees.

22. The illumination system as recited in claim 20, wherein the light emitting elements are selected from the group consisting of light emitting diodes, lasing diodes and combinations thereof.

23. A method of illumination of a target with light beams of different wavelength character for use in selective fluorescence or reflectance measurements of the target, the method comprising the steps of:
providing a plurality of selectively activatable light sources characterized by different intrinsic defined peak wavelength light emissions;
providing at least a first multi-branch solid light guide of unitary, hard plastic construction, the solid light guide comprising a main trunk, a plurality of proximal branches defining inlets adapted to receive the light emissions from the light sources, and at least one set of intermediate branches disposed between the proximal branches and the main trunk, wherein at least a first one of the proximal branches merges with a second one of the proximal branches to form a first intermediate branch and at least a third one of the proximal branches merges with a fourth one of the proximal branches to form a second intermediate branch, wherein light emissions transmitted by the first one of the proximal branches are combined with the light emissions transmitted by the second one of the proximal branches within the first intermediate branch and wherein light emissions transmitted by the third one of the proximal branches are combined with the light emissions transmitted by the fourth one of the proximal branches within the second intermediate branch such that the intermediate branches carry combined light emissions from the proximal branches towards the main trunk;

operatively connecting an imaging or optical device to the main trunk for transmission of coaligned light emissions from the light sources at a magnified power level of not less than 20 mW, the magnified power level being greater than the power level of the light emissions from the individual selectively activatable light sources and wherein the magnified power level is suitable for selective fluorescence or reflectance measurements of the target;

selectively activating the light sources to illuminate the target with a series of light beams of different defined wavelength character; and recording the fluorescence and/or fluorescence decay and/or reflectance characteristics of the target at the different applied wavelengths.

\* \* \* \* \*